(12) United States Patent
Lee

(10) Patent No.: US 11,464,678 B1
(45) Date of Patent: Oct. 11, 2022

(54) GOGGLE LENS SUITABLE FOR GOLFERS TO WEAR ALL-WEATHER AND METHOD OF MANUFACTURING THE SAME

(71) Applicant: Chun Sing Lee, Hong Kong (CN)

(72) Inventor: Chun Sing Lee, Hong Kong (CN)

( * ) Notice: Subject to any disclaimer, the term of this patent is extended or adjusted under 35 U.S.C. 154(b) by 0 days.

(21) Appl. No.: 17/712,166

(22) Filed: Apr. 3, 2022

(51) Int. Cl.
| | |
|---|---|
| *A61F 9/02* | (2006.01) |
| *B29C 45/00* | (2006.01) |
| *B29C 45/16* | (2006.01) |
| *G02B 1/04* | (2006.01) |
| *G02B 1/11* | (2015.01) |
| *B29L 11/00* | (2006.01) |

(52) U.S. Cl.
CPC .......... *A61F 9/022* (2013.01); *B29C 45/0001* (2013.01); *B29C 45/1679* (2013.01); *G02B 1/041* (2013.01); *G02B 1/11* (2013.01); *B29K 2995/003* (2013.01); *B29K 2995/0021* (2013.01); *B29K 2995/0026* (2013.01); *B29L 2011/0016* (2013.01)

(58) Field of Classification Search
CPC . A61F 9/022; B29C 45/0001; B29C 45/1679; G02B 1/041; G02B 1/11; B29K 2995/0021; B29K 2995/0026; B29K 2995/003; B29L 2011/0016
See application file for complete search history.

(56) References Cited

U.S. PATENT DOCUMENTS

2014/0233105 A1* 8/2014 Schmeder ............... G02C 7/12
359/590

FOREIGN PATENT DOCUMENTS

| CN | 207401003 U | * | 5/2018 |
|---|---|---|---|
| CN | 111929924 A | * | 11/2020 |

* cited by examiner

*Primary Examiner* — Mustak Choudhury
(74) *Attorney, Agent, or Firm* — Li & Cai Intellectual Property (USA) Office

(57) ABSTRACT

A goggle lens suitable for golfers to wear all-weather and a method of manufacturing the same are provided. The goggle lens comprises: a substrate, by weight, comprising: 1000 parts of resin, 0.038998 parts of yellow pigment, 0.041715 parts of green pigment, 0.014272 parts of blue pigment, 0.024569 parts of purple pigment, 0.0021 parts of orange pigment, and 0.010859 parts each of 580 nm light absorber and 490 nm light absorber; a high-reflection layer arranged on one surface of the substrate that is adapted to be away from eyes of the golfer; an anti-reflection layer arranged on another surface of the substrate that is adapted to be adjacent to the eyes of the golfer; two hardened layers arranged between the high-reflection layer and the substrate, and between the anti-reflection layer and the substrate; and one photocatalytic antibacterial layer; wherein a light transmittance of the goggle lens is between 27% and 29%.

9 Claims, 7 Drawing Sheets

| amorphous tetrahedral carbon layer |
| :---: |
| photocatalytic antibacterial layer |
| silicon dioxide sub-layers |
| titanium pentoxide sub-layer |
| silicon dioxide sub-layers |
| titanium pentoxide sub-layer |
| silicon dioxide sub-layers |
| hardening layer |
| substrate |
| hardening layer |
| silicon dioxide sub-layers |
| titanium pentoxide sub-layer |
| silicon dioxide sub-layers |
| titanium pentoxide sub-layer |
| silicon dioxide sub-layers |
| titanium pentoxide sub-layer |
| silicon dioxide sub-layers |
| photocatalytic antibacterial layer |
| amorphous tetrahedral carbon layer |

Rows 3–7 are bracketed as "high-reflection layer"; rows 10–16 are bracketed as "anti-reflection layer".

FIG. 4

| hydrophobic and oleophobic layer |
|:---:|
| photocatalytic antibacterial layer |
| silicon dioxide sub-layers |
| titanium pentoxide sub-layer |
| silicon dioxide sub-layers |
| titanium pentoxide sub-layer |
| silicon dioxide sub-layers |
| hardening layer |
| substrate |
| hardening layer |
| silicon dioxide sub-layers |
| titanium pentoxide sub-layer |
| silicon dioxide sub-layers |
| titanium pentoxide sub-layer |
| silicon dioxide sub-layers |
| titanium pentoxide sub-layer |
| silicon dioxide sub-layers |
| photocatalytic antibacterial layer |
| hydrophobic and oleophobic layer |

Rows 3–7 form the high-reflection layer. Rows 11–17 form the anti-reflection layer.

FIG. 6

GOGGLE LENS SUITABLE FOR GOLFERS TO WEAR ALL-WEATHER AND METHOD OF MANUFACTURING THE SAME

FIELD OF THE DISCLOSURE

The present disclosure relates to the technical field of goggle lenses, in particular, to a goggle lens suitable for golfers to wear all-weather and a method of manufacturing the same.

BACKGROUND OF THE DISCLOSURE

Most of the existing sun protection glasses are general-purpose sun protection glasses, which only have the functions of anti-100% UV400, anti-blue light of about 30-50%, and dimming the light. Some known sunglasses dedicated to golf also have the following shortcomings. 1. The scope of application is narrow, some are only suitable for use in strong sunlight, some are only suitable for use in cloudy days, and the narrow scope of application makes users need to purchase many kinds of goggles, and it is inconvenient to carry and store. 2. Poor color matching and poor visual comfort. Bright color matching is often used, which will make the golfer in a state of excitement for 4-5 hours on the court, but the excited state not only affects the performance of the player's skills, but also increases the player's fatigue after the game. 3. The stray light filtering effect is poor, which will affect the golfer's ability to distinguish the ups and downs, grass grain and slope of the green. 4. If the golfer wears it for a long time, the bacteria on the goggle lens can easily spread to the eyes and cause infection.

SUMMARY OF THE DISCLOSURE

The purpose of the present disclosure is to provide a goggle lens suitable for golfers to wear all-weather, so as to solve at least one of the above-mentioned defects existing in the related art at least to a certain extent.

In order to achieve the aforementioned purpose, the present disclosure provides a goggle lens suitable for golfers to wear all-weather, wherein the goggle lens comprises: a substrate, wherein by weight, a composition of the substrate comprises 1000 parts of resin, 0.038998 parts of yellow pigment, 0.041715 parts of green pigment, 0.014272 parts of blue pigment, 0.024569 parts of purple pigment, 0.0021 parts of orange pigment, and 0.010859 parts each of 580 nm light absorber and 490 nm light absorber; a high-reflection layer arranged on one surface of the substrate that is adapted to be away from eyes of the golfer; an anti-reflection layer arranged on another surface of the substrate that is adapted to be adjacent to the eyes of the golfer; two hardened layers respectively arranged between the high-reflection layer and the substrate, and between the anti-reflection layer and the substrate; and at least one photocatalytic antibacterial layer; wherein a light transmittance of the goggle lens is between 27% and 29%.

Preferably, the goggle lens further comprises two amorphous tetrahedral carbon layers, the two amorphous tetrahedral carbon layers are arranged on two surfaces of the goggle lens, and a thickness of each of the two amorphous tetrahedral carbon layers is between 70 nanometers and 120 nanometers. The thickness of the amorphous tetrahedral carbon layer can be, for example, 75 nanometers, 80 nanometers, 85 nanometers, 90 nanometers, 100 nanometers, 110 nanometers, etc. Preferably, the photocatalytic antibacterial layer is adjacent to one of the two amorphous tetrahedral carbon layers.

Preferably, the goggle lens further comprises two hydrophobic and oleophobic layers, the two hydrophobic and oleophobic layers are respectively arranged on two surfaces of the goggle lens, and a thickness of each of the two hydrophobic and oleophobic layers is between 80 nanometers and 200 nanometers. The thickness of the hydrophobic and oleophobic layer can be, for example, 85 nanometers, 90 nanometers, 95 nanometers, 100 nanometers, 120 nanometers, 130 nanometers, 140 nanometers, 150 nanometers, 170 nanometers, 180 nanometers, etc. Preferably, the photocatalytic antibacterial layer is adjacent to one of the two hydrophobic and oleophobic layers.

Preferably, a material of the photocatalytic antibacterial layers is a nanoscale inorganic antibacterial agent.

Preferably, the high-reflection layer comprises three silicon dioxide sub-layers, a titanium pentoxide sub-layer is arranged between any two silicon dioxide sub-layers, and a total thickness of the high-reflection layer is between 1200 nanometers and 2700 nanometers. For example, it can be 1300 nanometers, 1500 nanometers, 1800 nanometers, 2000 nanometers, 2400 nanometers, 2600 nanometers, and the like. The anti-reflection layer comprises four silicon dioxide sub-layers, a titanium pentoxide sub-layer is arranged between any two silicon dioxide sub-layers, and a total thickness of the anti-reflection layer is between 750 nanometers and between 880 nm. For example, it can be 760 nanometers, 780 nanometers, 800 nanometers, 830 nanometers, 850 nanometers, 860 nanometers, and the like.

The present disclosure provides a method of manufacturing a lens, comprising: Step S1: manufacturing a resin substrate; Step S1-1: drying a raw material at 120° C. for 4 hours; Step S1-2: color matching; and by weight, weighing and stirring well the following raw materials: 1000 parts of resin, 0.038998 parts of yellow pigment, 0.041715 parts of green pigment, 0.014272 parts of blue pigment, 0.024569 parts of purple pigment, 0.0021 parts of orange pigment, and 0.010859 parts each of 580 nm light absorber and 490 nm light absorber; Step S1-3: injection molding; injection molding at 280° C. to 290° C.; Step S1-4: cleaning; performing ultrasonic cleaning twice in 60° C. pure water for 1200 seconds each time; Step S1-5: strengthening; soaking for 30 minutes under conditions of an ambient temperature of 18° C., a liquid temperature of 15° C., and a humidity of not more than 45%; Step S1-6: pre-drying; pre-drying at 70° C. for 20 to 30 minutes; Step S1-7: quality inspecting; Step S1-8: drying; drying at 120° C. for 3 hours, and releasing from an oven to obtain a resin substrate; Step S2: dipping and curing, then forming a hardened layer on a surface of the resin substrate; wherein a manufactured resin substrate is dipped in a treatment solution, pulled up, and then dried at 60° C. for 2 hours to obtain a resin substrate with two hardened layers formed on two surfaces thereof; Step S3: cleaning and destaticizing; soaking the resin substrate with a deionized water, cleaning the resin substrate ultrasonic waves, then drying the resin substrate with nitrogen, and finally scanning a surface of the resin substrate evenly with a static elimination gun; Step S4: cleaning and roughening; placing the resin substrate on a coating rack in a vacuum chamber, performing glow discharging for 12 minutes in a $7 \times 10^{-5}$ Pa argon atmosphere, and the substrate being bombarded by ions to obtain cleaning and roughening effects; Step S5: evaporating and forming a high-reflection layer, an anti-reflection layer and two photocatalytic antibacterial layers; using an electron gun to alternately evaporate a silicon dioxide sub-layer and a titanium pentoxide sub-layer on one of the two hardened layers of the substrate to form a high-reflection layer in a $3.5\times10^{-5}$ Pa oxygen atmosphere; using the electron gun to alternately evaporate the silicon dioxide sub-layer and the titanium pentoxide sub-layer on another one of the two hardened layers of the resin substrate to form an anti-reflection layer in a $3.5\times10^{-5}$ Pa oxygen atmosphere; and using an electron gun to alternately evaporate the high-reflection layer and the anti-reflection layer to respectively form two photocatalytic antibacterial layers in a $3.5\times10^{-5}$ Pa oxygen atmosphere, so to obtain a lens.

Preferably, the method, after S5, further comprises: S6: forming an amorphous tetrahedral carbon layer on each of the two photocatalytic antibacterial layers; discharging in a $2\times10^{-2}$ Pa atmosphere, wherein carbon atoms and carbon molecules are vaporized on a surface of a graphite electrode and ionized to form carbon ions, the carbon atoms and carbon molecules are filtered out by a magnetic filter device, and the filtered carbon ions are deposited on the goggle lens to form an amorphous tetrahedral carbon film on the two surfaces of the goggle lens.

Preferably, the method, after S5, further comprises: Step S7: evaporating and forming two hydrophobic and oleophobic layers respectively on the two photocatalytic antibacterial layers; using the electron gun to evaporate a hydrophobic and oleophobic material on each of the two photocatalytic antibacterial layers to form the hydrophobic and oleophobic layer in a $3.5\times10^{-5}$ Pa oxygen atmosphere.

Compared with the prior art, the present disclosure has at least the following beneficial effects.

On the one hand, the light transmittance of the goggle lens is 27% to 29%, so that the light source reflected on the ground between 10 lumens and 6000 lumens does not affect vision, and can adapt to all-day lighting environment; on the other hand, the unique color formula will not make the golfer excited, and can make the golfer feel in the natural grassland and relax. Therefore, this lens is suitable for golfers to wear all day long.

The goggle lens contains two light absorbers of 580 nm and 490 nm, which can make red, green, yellow and blue colors more vivid and increase visual clarity; in addition, it can prevent 100% UV400 and 94% UV420, so as to better protect the eyes.

The goggle lens contains at least one photocatalytic anti-bacterial layer, which can slowly release antibacterial ingredients under light irradiation and can prevent bacteria from growing on the surface of the goggle lens.

The goggle lens contains a high-reflection layer and an anti-reflection layer. The anti-reflection layer can directly penetrate the goggle lens from the rear to avoid being reflected by the goggle lens and enter the eyes; the high-reflection layer can block most of the reflections that blur objects and images, the combination of the two solves the visual difference caused by the non-absolute plane surface of the object, resulting in multi-angle and different reflectivity reflections, so that the wearer can see the object more clearly and three-dimensionally and the golfer can better distinguish the undulations, grass patterns and slopes of the ridge.

The surface of the goggle lens contains an amorphous tetrahedral carbon layer, and the high hardness and corrosion resistance of the amorphous tetrahedral carbon make the goggle lens have better wear resistance and corrosion resistance.

The surface of the goggle lens contains a hydrophobic and oleophobic layer, which makes it difficult to form water mist on the surface of the goggle lens.

The above-mentioned lens manufacturing process includes a cleaning step, a static elimination step, and a roughening step before the film is formed on the surface of the substrate, so that the film layer and the substrate are combined more firmly, and the yield rate is higher.

BRIEF DESCRIPTION OF THE DRAWINGS

FIG. 4 is a schematic structural diagram of a lens of the second embodiment.
FIG. 6 is a schematic structural diagram of a lens of the third embodiment.

DETAILED DESCRIPTION OF THE EXEMPLARY EMBODIMENTS

The present disclosure will be further described below with reference to the accompanying drawings and embodiments.

Figure 1:
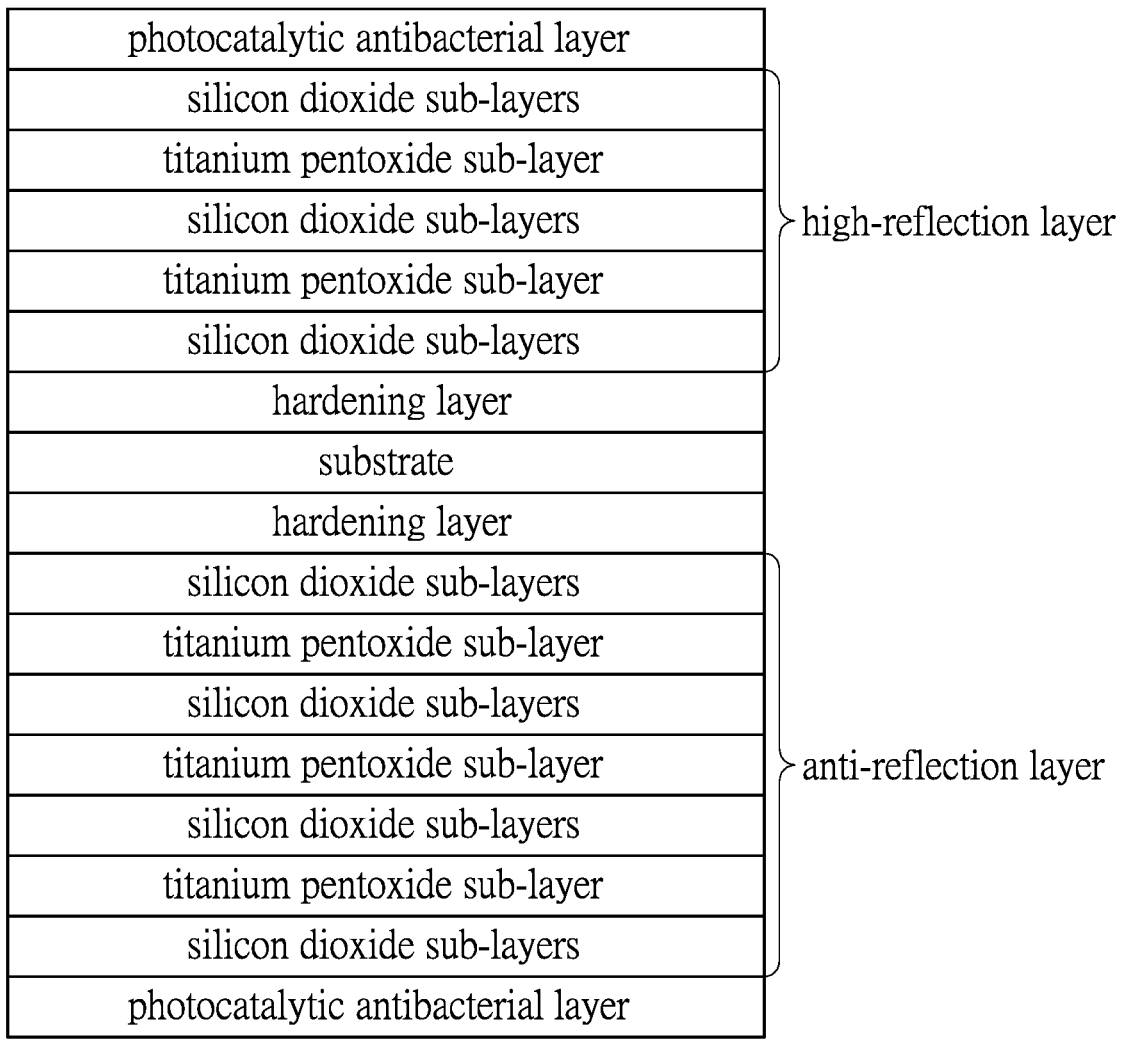
FIG. 1 is a schematic diagram of the structure of a lens of the first embodiment.

FIG. 1 shows the structure of the goggle lens of the first embodiment. As shown in FIG. 1, the goggle lens includes a substrate, two surfaces of the substrate are provided with hardened layers, one of the hardened layers is provided with a high-reflection layer, and the other hardened layer is provided with an anti-reflection layer. Both the high-reflection layer and the anti-reflection layer are provided with a photocatalytic antibacterial layer.

The substrate, by weight, comprises a composition as follows: 1000 parts of resin, 0.038998 parts of yellow pigment (Code 8416), 0.041715 parts of green pigment (Code 9002), 0.014272 parts of blue pigment (Code 634), 0.024569 parts of purple pigment (Code 4410), 0.0021 parts of orange pigment (Code 8404), and 0.010859 parts each of 580 nm light absorber and 490 nm light absorber. The resin is preferably polycarbonates. The 580 nm light absorber is preferably a 580 nm light absorber from LANXESS, Germany, and its main component is a polymer phthalocyanine compound. The 490 nm light absorber is preferably a 490 nm light absorber from LANXESS, Germany, and its main component is a polymer azo nickel metal compound.

The hardened layer is used to improve the hardness of the goggle lens. In this embodiment, the HC-3800 material produced by Japan Seiko is selected, and the main component is organic silicon.

The high-reflection layer includes five sub-layers, of which three are silicon dioxide sub-layers and of which two are titanium pentoxide sub-layers. The silicon dioxide sub-layers and the titanium pentoxide sub-layers are alternately arranged, and the silicon dioxide sub-layers are combined with the hardened layer of the substrate. The sum of the thicknesses of the five sub-layers of the high-reflection layer is 1500 nanometers. In application, the surface of the goggle lens is provided with a high-reflection layer away from the eyes.

The anti-reflection layer includes seven sub-layers, of which four are silicon dioxide sub-layers and of which three are titanium pentoxide sub-layers. The silicon dioxide sub-layers and the titanium pentoxide sub-layers are alternately arranged, and the silicon dioxide sub-layers are combined with the hardened layer of the substrate. The sum of the thicknesses of the five sub-layers of the high-reflection layer is 1500 nanometers. In application, the surface of the goggle lens is provided with a high-reflection layer away from the eyes.

The photocatalytic antibacterial layer is a titanium dioxide layer, wherein the titanium dioxide material is a nanoscale material, and the thickness of the photocatalytic antibacterial layer is 100 nanometers. The material of the photocatalytic antibacterial layer of the present disclosure is not limited to titanium dioxide. The material of the photocatalytic antibacterial layer of the present disclosure is preferably a nanoscale inorganic antibacterial agent.

Figure 2:
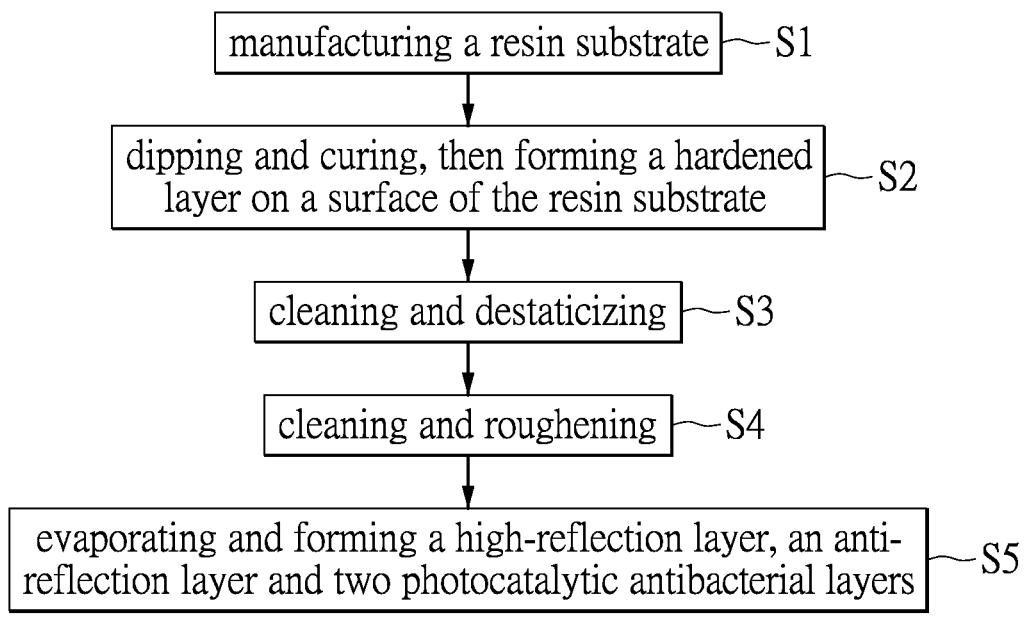
FIG. 2 is a flow chart of a manufacturing process.
Figure 3:
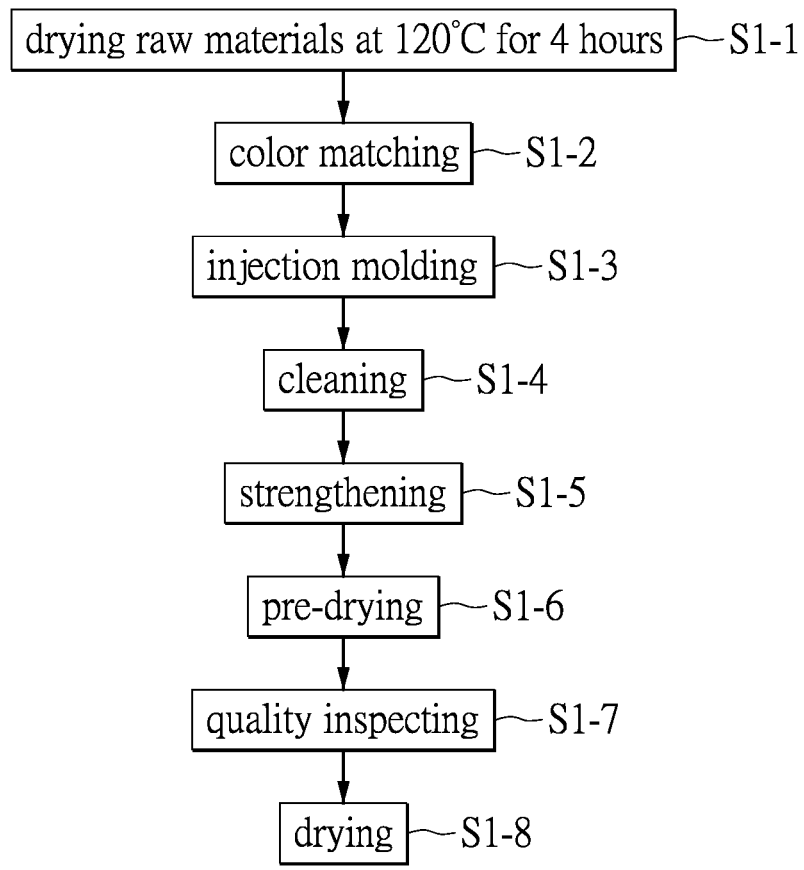
FIG. 3 is a flow chart of a manufacturing process of a substrate.

FIG. 2 is a flow chart of a manufacturing process, and FIG. 3 is a flow chart of a manufacturing process of a substrate. Specifically, a method of manufacturing a lens, comprises:

Step S1: manufacturing a resin substrate;

Step S1-1: drying a raw material at 120° C. for 4 hours;

Step S1-2: color matching; and by weight, weighing and stirring well the following raw materials: 1000 parts of resin, 0.038998 parts of yellow pigment, 0.041715 parts of green pigment, 0.014272 parts of blue pigment, 0.024569 parts of purple pigment, 0.0021 parts of orange pigment, and 0.010859 parts each of 580 nm light absorber and 490 nm light absorber;

Step S1-3: injection molding; injection molding at 280° C. to 290° C.;

Step S1-4: cleaning; performing ultrasonic cleaning twice in 60° C. pure water for 1200 seconds each time;

Step S1-5: strengthening; soaking for 30 minutes under conditions of an ambient temperature of 18° C., a liquid temperature of 15° C., and a humidity of not more than 45%;

Step S1-6: pre-drying; pre-drying at 70° C. for 20 to 30 minutes;

Step S1-7: quality inspecting;

Step S1-8: drying; drying at 120° C. for 3 hours, and releasing from an oven to obtain a resin substrate;

Step S2: dipping and curing, then forming a hardened layer on a surface of the resin substrate; wherein a manufactured resin substrate is dipped in a treatment solution, pulled up, and then dried at 60° C. for 2 hours to obtain a resin substrate with two hardened layers formed on two surfaces thereof;

Step S3: cleaning and destaticizing; soaking the resin substrate with a deionized water, cleaning the resin substrate with ultrasonic waves, then drying the resin substrate with nitrogen, and finally scanning a surface of the resin substrate evenly with a static elimination gun;

Step S4: cleaning and roughening; placing the resin substrate on a coating rack in a vacuum chamber, performing glow discharging for 12 minutes in a $7 \times 10^{-5}$ Pa argon atmosphere, and the substrate being bombarded by ions to obtain cleaning and roughening effects; and Step S5: evaporating and forming a high-reflection layer, an anti-reflection layer and two photocatalytic antibacterial layers; using an electron gun to alternately evaporate a silicon dioxide sub-layer and a titanium pentoxide sub-layer on one of the two hardened layers of the substrate to form a high-reflection layer in a $3.5 \times 10^{-5}$ Pa oxygen atmosphere; using the electron gun to alternately evaporate the silicon dioxide sub-layer and the titanium pentoxide sub-layer on another one of the two hardened layers of the resin substrate to form an anti-reflection layer in a $3.5 \times 10^{-5}$ Pa oxygen atmosphere; and using an electron gun to alternately evaporate the high-reflection layer and the anti-reflection layer to respectively form two photocatalytic antibacterial layers in a $3.5 \times 10^{-5}$ Pa oxygen atmosphere, so to obtain a lens.

The goggle lens of this embodiment has the following advantages.

The light transmittance of the goggle lens is 27% to 29%, so that the light source reflected on the ground between 10 lumens and 6000 lumens will not affect the vision, and can adapt to the all-weather lighting environment. The unique color formula will not make golfers excited, and it can make golfers feel in the natural grassland and relax. Therefore, this lens is suitable for golfers to wear all day long.

The goggle lens contains two light absorbers of 580 nm and 490 nm, which can make red, green, yellow and blue colors more vivid and increase visual clarity; in addition, it can prevent 100% UV400 and 94% UV420, so as to better protect the eyes.

The goggle lens contains at least one photocatalytic antibacterial layer, which can slowly release antibacterial ingredients under light irradiation and prevent bacteria from growing on the surface of the goggle lens. The goggle lens contains a high-reflection layer and an anti-reflection layer. The anti-reflection layer can directly penetrate the goggle lens from the rear to avoid being reflected by the goggle lens and enter the eyes. The high-reflection layer can block most of the reflections that blur objects and images. The combination of the two solves the visual difference caused by the non-absolute plane surface of the object, resulting in multi-angle and different reflectivity reflections, so that the wearer can see the object more clearly and three-dimensionally and the golfer can better distinguish the undulations, grass patterns and slopes of the ridge.

FIG. 4 is a schematic structural diagram of a lens of the second embodiment. As shown in FIG. 4, the goggle lens of the second embodiment includes a substrate, two surfaces of the substrate are provided with hardened layers, one of the hardened layers is provided with a high-reflection layer, and the other hardened layer is provided with an anti-reflection layer. The high-reflection layer and the anti-reflection layer are all provided with a photocatalytic antibacterial layer, and the photocatalytic antibacterial layer is all provided with an amorphous tetrahedral carbon layer.

The substrate, the hardened layer, the high-reflection layer, the anti-reflection layer, and the photocatalytic antibacterial layer are the same as those in the previous embodiment, and will not be repeated here.

The thickness of the amorphous tetrahedral carbon layer is 100 nm.

Figure 5:
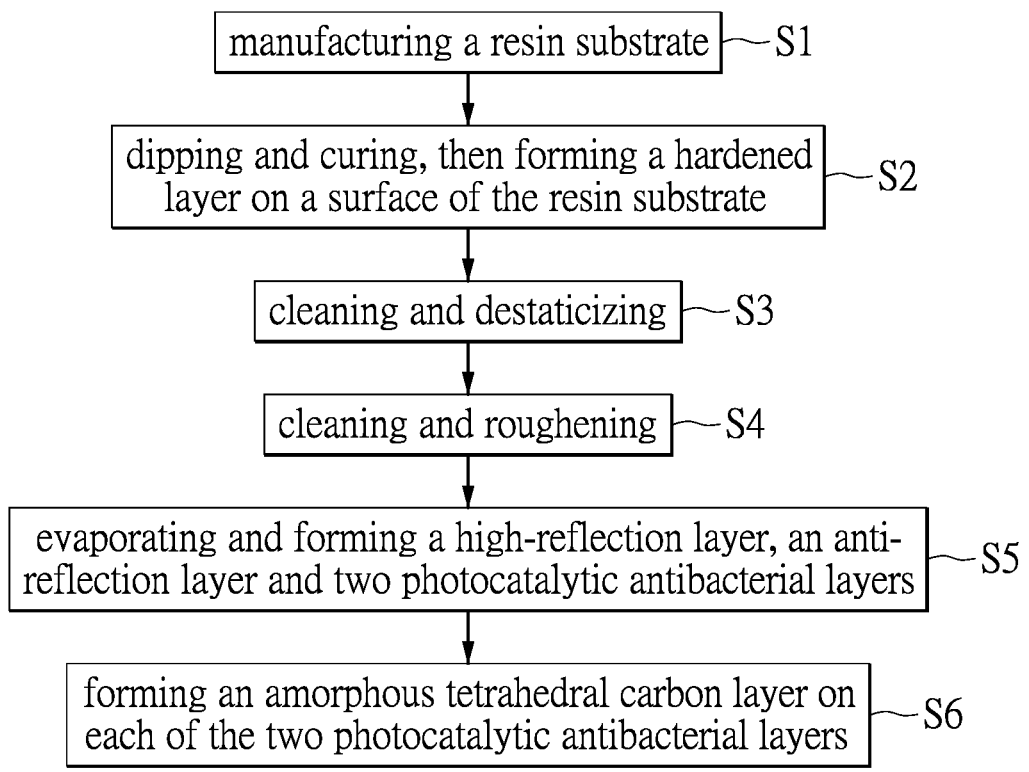
FIG. 5 is a flow chart of a manufacturing process of a lens of the second embodiment.

FIG. 5 is a flow chart of a manufacturing process of a lens of the second embodiment, and the manufacturing process comprises:

Step S1: manufacturing a resin substrate;

Step S2: dipping and curing, then forming a hardened layer on a surface of the resin substrate;

Step S3: cleaning and destaticizing;

Step S4: cleaning and roughening;

Step S5: evaporating and forming a high-reflection layer, an anti-reflection layer and at least one photocatalytic antibacterial layer; wherein the foregoing steps S1 to S5 are the same as the foregoing embodiments, and are not repeated here; and Step S6: forming an amorphous tetrahedral carbon layer on each of the two photocatalytic antibacterial layers; discharging in a $2 \times 10^{-2}$ Pa atmosphere, wherein carbon atoms and carbon molecules are vaporized on a surface of a graphite electrode and ionized to form carbon ions, the carbon atoms and carbon molecules are filtered out by a magnetic filter device, and the filtered carbon ions are deposited on the goggle lens to form an amorphous tetrahedral carbon film on the two surfaces of the goggle lens.

The goggle lens of the second embodiment has the characteristics of the goggle lens of the first embodiment, because the surface of the goggle lens is also provided with an amorphous tetrahedral carbon layer. The high hardness and corrosion resistance of the amorphous tetrahedral carbon make the goggle lens also have better wear resistance and corrosion resistance.

FIG. 6 is a schematic structural diagram of a lens of the third embodiment. As shown in FIG. 6, the goggle lens of the third embodiment includes a substrate, two surfaces of the substrate are provided with hardened layers, one of the hardened layers is provided with a high-reflection layer, and the other hardened layer is provided with an anti-reflection layer. The high-reflection layer and the anti-reflection layer are all provided with a photocatalytic antibacterial layer, and the photocatalytic antibacterial layer is provided with a hydrophobic and oleophobic layer.

The substrate, the hardened layer, the high-reflection layer, the anti-reflection layer, and the photocatalytic antibacterial layer are the same as those in the previous embodiment, and will not be repeated here.

The thickness of the hydrophobic and oleophobic layer is 120 nm. The material of the hydrophobic and oleophobic layer is preferably SH-HT material from the Don Co., Ltd., Korea, which is a fluorine-modified polymer nanomaterial containing active siloxane groups.

Figure 7:
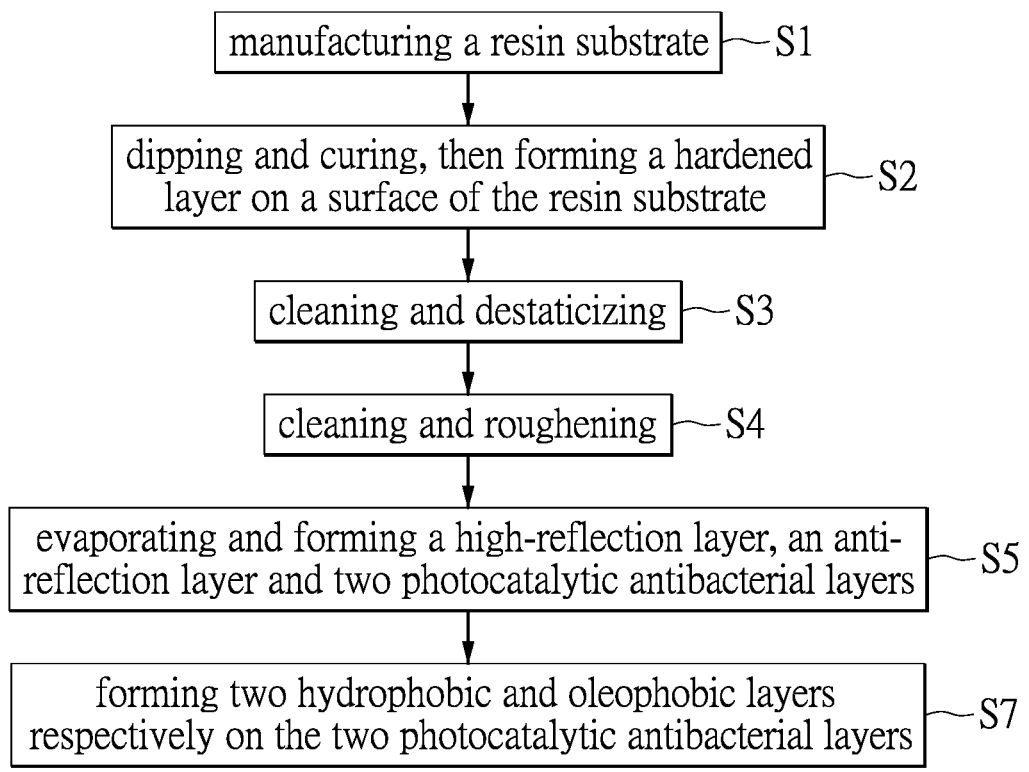
FIG. 7 is a flow chart of a manufacturing process of a lens of the third embodiment.

FIG. 7 is a flow chart of a manufacturing process of a lens of the third embodiment, and the manufacturing method comprises:

Step S1: manufacturing a resin substrate;

Step S2: dipping and curing, then forming a hardened layer on a surface of the resin substrate;

Step S3: cleaning and destaticizing;

Step S4: cleaning and roughening;

Step S5: evaporating and forming a high-reflection layer, an anti-reflection layer and at least one photocatalytic antibacterial layer; wherein the foregoing steps S1 to S5 are the same as the foregoing embodiments, and are not repeated here; and Step S7: evaporating and forming two hydrophobic and oleophobic layers respectively on the two photocatalytic antibacterial layers in a $3.5 \times 10^{-5}$ Pa oxygen atmosphere, and using an electron gun to evaporate the hydrophobic and oleophobic material on the photocatalytic antibacterial layer to form a hydrophobic and oleophobic layer.

In addition to the characteristics of the goggle lens of the first embodiment, the goggle lens of the third embodiment is also provided with a hydrophobic and oleophobic layer on its surface, so that water mist is not easily formed on the surface of the goggle lens.

In the first embodiment, the photocatalytic antibacterial layer is arranged on the surface of the goggle lens. In the second embodiment, the surface of the goggle lens is an amorphous tetrahedral carbon layer, and the photocatalytic antibacterial layer is adjacent to the amorphous tetrahedral carbon layers. In the third embodiment, the surface of the goggle lens is a hydrophobic and oleophobic layer, and the photocatalytic antibacterial layer is adjacent to the hydrophobic and oleophobic layers. In these structures, the antibacterial ingredients released by the photocatalytic antibacterial layer are more likely to reach the surface of the goggle lens. However, the position of the photocatalytic antibacterial layer in the present disclosure is not limited by this.

In method of manufacturing the goggle lens of the above embodiment, the cleaning step, the static electricity elimination step, and the roughening step are included before the film is formed on the surface of the substrate, so that the film layer and the substrate are combined more firmly and the yield is higher. The manufacture of the goggle lenses of the present disclosure is not limited to these methods.

The above is only a preferred embodiment of the present disclosure, and is not intended to limit the present disclosure. Any modification, equivalent replacement or improvement made within the spirit and principle of the present disclosure shall be included in the protection scope of the present disclosure.

What is claimed is:

1. A goggle lens suitable for a golfer to wear all-weather, comprising:
    a substrate, wherein, by weight, a composition of the substrate includes 1000 parts of resin, 0.038998 parts of yellow pigment, 0.041715 parts of green pigment, 0.014272 parts of blue pigment, 0.024569 parts of purple pigment, 0.0021 parts of orange pigment, and 0.010859 parts of each of 580 nm light absorber and 490 nm light absorber;
    a high-reflection layer arranged on one surface of the substrate that is adapted to be away from eyes of the golfer;
    an anti-reflection layer arranged on another surface of the substrate that is adapted to be adjacent to the eyes of the golfer;
    two hardened layers respectively arranged between the high-reflection layer and the substrate, and between the anti-reflection layer and the substrate;
    at least one photocatalytic antibacterial layer; and
    two amorphous tetrahedral carbon layers;
    wherein the two amorphous tetrahedral carbon layers are arranged on two surfaces of the goggle lens, and a thickness of each of the two amorphous tetrahedral carbon layers is between 70 nanometers and 120 nanometers;
    wherein a light transmittance of the goggle lens is between 27% and 29%.

2. The goggle lens according to claim 1, wherein the at least one photocatalytic antibacterial layer is adjacent to one of the two amorphous tetrahedral carbon layers.

3. The goggle lens according to claim 1, further comprising;
    two hydrophobic and oleophobic layers;
    wherein the two hydrophobic and oleophobic layers are respectively arranged on two surfaces of the goggle lens, and a thickness of each of the two hydrophobic and oleophobic layers is between 80 nanometers and 200 nanometers.

4. The goggle lens according to claim 3, wherein the at least one photocatalytic antibacterial layer is adjacent to one of the two hydrophobic and oleophobic layers.

5. The goggle lens according to claim 1, wherein a material of the at least one photocatalytic antibacterial layers is a nanoscale inorganic antibacterial agent.

6. The goggle lens according to claim 1, wherein the high-reflection layer includes three silicon dioxide sub-layers, a titanium pentoxide sub-layer is arranged between any two silicon dioxide sub-layers, and a total thickness of the high-reflection layer is between 1200 nanometers and 2700 nanometers;
    wherein the anti-reflection layer includes four silicon dioxide sub-layers, a titanium pentoxide sub-layer is arranged between any two silicon dioxide sub-layers, and a total thickness of the anti-reflection layer is between 750 nanometers and between 880 nm.

7. A method of manufacturing a lens, comprising the following steps:
Step S1: manufacturing a resin substrate;
　Step S1-1: drying raw materials at 120° C. for 4 hours;
　Step S1-2: color matching
　　by weight, weighing and stirring well the following raw materials: 1000 parts of resin, 0.038998 parts of yellow pigment, 0.041715 parts of green pigment, 0.014272 parts of blue pigment, 0.024569 parts of purple pigment, 0.0021 parts of orange pigment, and 0.010859 parts each of 580 nm light absorber and 490 nm light absorber;
　Step S1-3 : injection molding
　　injection molding at 280° C. to 290° C.;
　Step S1-4: cleaning
　　performing ultrasonic cleaning twice in 60° C. pure water for 1200 seconds each time;
　Step S1-5: strengthening
　　soaking for 30 minutes under conditions of an ambient temperature of 18° C., a liquid temperature of 15° C., and a humidity of not more than 45%;
　Step S1-6: pre-drying
　　pre-drying at 70° C. for 20 to 30 minutes;
　Step S1-7: quality inspecting
　Step S1-8: drying
　　drying at 120° C. for 3 hours, and releasing from an oven to obtain a resin substrate;
Step S2: dipping and curing, then forming a hardened layer on a surface of the resin substrate;
　wherein a manufactured resin substrate is dipped in a treatment solution, pulled up, and then dried at 60° C. for 2 hours to obtain a resin substrate with two hardened layers formed on two surfaces thereof;
Step S3: cleaning and destaticizing
　soaking the resin substrate with a deionized water, cleaning the resin substrate with ultrasonic waves, then drying the resin substrate with nitrogen, and finally scanning a surface of the resin substrate evenly with a static elimination gun;
Step S4: cleaning and roughening
　placing the resin substrate on a coating rack in a vacuum chamber, performing glow discharging for 12 minutes in a $7\times10^{-5}$ Pa argon atmosphere, and the resin substrate being bombarded by ions to obtain cleaning and roughening effects;
Step S5: evaporating and forming a high-reflection layer, an anti-reflection layer and two photocatalytic antibacterial layers;
　using an electron gun to alternately evaporate a silicon dioxide sub-layer and a titanium pentoxide sub-layer on one of the two hardened layers of the resin substrate to form a high-reflection layer in a $3.5\times10^{-5}$ Pa oxygen atmosphere;
　using the electron gun to alternately evaporate the silicon dioxide sub-layer and the titanium pentoxide sub-layer on another one of the two hardened layers of the resin substrate to form an anti-reflection layer in a $3.5\times10^{-5}$ Pa oxygen atmosphere; and
　using an electron gun to alternately evaporate the high-reflection layer and the anti-reflection layer to respectively form the two photocatalytic antibacterial layers in a $3.5\times10^{-5}$ Pa oxygen atmosphere, so to obtain a lens.

8. The method according to claim 7, wherein, after Step S5, further comprising:
　Step S6: forming an amorphous tetrahedral carbon layer on each of the two photocatalytic antibacterial layers;
　discharging in a $2\times10^{-2}$ Pa atmosphere, wherein carbon atoms and carbon molecules are vaporized on a surface of a graphite electrode and ionized to form carbon ions, the carbon atoms and carbon molecules are filtered out by a magnetic filter device, and the filtered carbon ions are deposited on the goggle lens to form an amorphous tetrahedral carbon film on the two surfaces of the goggle lens.

9. The method according to claim 7, wherein, after Step S5, further comprising:
　Step S7: evaporating and forming two hydrophobic and oleophobic layers respectively on the two photocatalytic antibacterial layers;
　using the electron gun to evaporate a hydrophobic and oleophobic material on each of the two photocatalytic antibacterial layers to form the hydrophobic and oleophobic layer in a $3.5\times10^{-5}$ Pa oxygen atmosphere.

* * * * *